United States Patent
Benderly et al.

(10) Patent No.: US 7,393,976 B2
(45) Date of Patent: Jul. 1, 2008

(54) PROCESS FOR MANUFACTURING REDUCED WATER CONTENT (METH)ACRYLIC ACID

(75) Inventors: Abraham Benderly, Elkins Park, PA (US); Michael Stanley DeCourcy, Houston, TX (US); Alan Sopchik, Webster, TX (US)

(73) Assignee: Rohm and Haas Company, Philadelphia, PA (US)

( * ) Notice: Subject to any disclaimer, the term of this patent is extended or adjusted under 35 U.S.C. 154(b) by 233 days.

(21) Appl. No.: 10/978,855

(22) Filed: Nov. 1, 2004

(65) Prior Publication Data

US 2005/0113605 A1    May 26, 2005

Related U.S. Application Data

(60) Provisional application No. 60/525,258, filed on Nov. 26, 2003.

(51) Int. Cl.
*C07C 51/42* (2006.01)

(52) U.S. Cl. ..................... 562/600
(58) Field of Classification Search ........... 562/598, 562/600, 523, 532; 560/218
See application file for complete search history.

(56) References Cited

U.S. PATENT DOCUMENTS 5,571,386 A * 11/1996 Bauer et al. ............. 203/38

* cited by examiner

*Primary Examiner*—Karl Puttlitz
(74) *Attorney, Agent, or Firm*—Marcella M. Bodner

(57) ABSTRACT

A method is provided herein for purifying (meth)acrylic acid to provide a purified (meth)acrylic acid product having a low aldehyde concentration and not more than 0.2 wt % water. One embodiment of the method includes distilling (meth) acrylic acid in the presence of an aldehyde treating compound. Another embodiment of the method includes also distilling crude (meth)acrylic acid in the presence of a reactive drying agent. (Meth)acrylic acid produced in this manner is especially suitable for use in specialty (meth)acrylic acid polymers, such as for example superabsorbent polymers, binders, and ethylene-(M)AA copolymers.

13 Claims, 1 Drawing Sheet

PROCESS FOR MANUFACTURING REDUCED WATER CONTENT (METH)ACRYLIC ACID

CROSS REFERENCE TO RELATED PATENT APPLICATIONS

Figure 1:
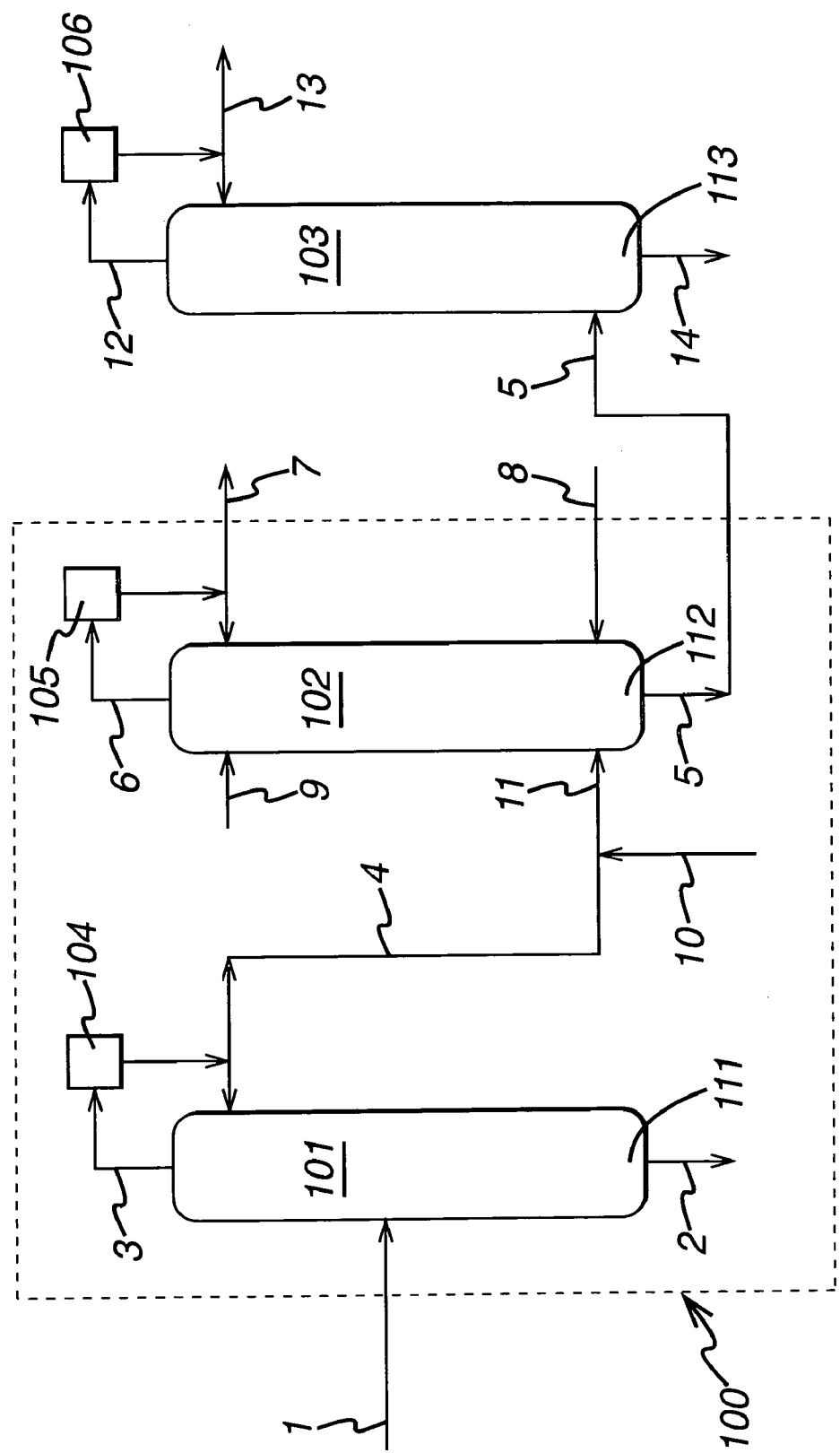

This is a non-provisional patent application which claims priority from U.S. provisional patent application Ser. No. 60/525,258, filed Nov. 26, 2003.

The present invention is related to a process for the production of substantially pure (meth)acrylic acid having a low water content and a low aldehyde content.

Residual impurities in (meth)acrylic acid (M)AA), particularly aldehydes and water, interfere with polymerization reactions thereby adversely impacting polymer properties. (M)AA having low aldehyde and low water levels is useful in producing specialty polymer compositions, for example, superabsorbent polymers, acrylic binders, ethylene-(M)AA copolymers, and polymers efficient as dispersants for oil well drilling muds and as flocculating agents. It would therefore be advantageous to specialty polymer manufacturers if (M)AA with both a low aldehyde content and a low water content could be economically and reliably produced. Although distillation processes capable of producing low aldehyde grades of (M)AA are known, such processes have heretofore been unable to reliably and economically provide both the low aldehyde and the low water levels that are desired in specialty polymer production. Further, as will be discussed in more detail below, it has been discovered that the addition of (meth) acrylic anhydrides is not an effective means for improving water removal in crude (meth)acrylic acid distillation systems. This is in spite of the fact that these compounds are inherently compatible with purified (meth)acrylic acid and are capable of absorbing moisture.

Generally, crude acrylic acid production processes include a first step of producing a mixed gas stream comprising acrylic acid which may be obtained, for example, without limitation, by catalytic gas phase oxidation of propane, propylene and/or acrolein with a molecular oxygen-containing gas. Similarly, for crude methacrylic acid producing processes, a mixed gas stream comprising methacrylic acid may be produced, for example, without limitation, by catalytic gas phase oxidation of at least one compound selected from the group consisting of isobutane, isobutylene, t-butyl alcohol, and methacrolein with a molecular oxygen-containing gas. A (meth)acrylic acid mixed gas stream produced by any one of various known processes, including, but not limited to either of the aforesaid oxidation steps, is then fed to a (M)AA collection column wherein a (M)AA containing solution is collected. Such solutions typically comprise water and other impurities such as (meth)acrolein, furfural, maleic acid, and acetic acid. The (meth)acrylic acid-containing solution is separated and purified in one or more distillation columns to remove substantial amounts of (meth)acrolein, acetic acid, and water, resulting in a crude (M)AA product that is typically about 90% pure and suitable for use in producing (meth) acrylic esters.

The crude (M)AA can be further purified through methods such as distillation to form distilled grades of (M)AA. In particular, such distilled grades of (M)AA have both reduced water levels and reduced aldehyde levels. Aldehyde species which may be present in acrylic acid may include but are not limited to acrolein, maleic anhydride, and furfural. Similar impurities may be present in niethacrylic acid (e.g., methacrolein and furfural). Heretofore disclosed distillation methods have not achieved both the low water concentrations and the low aldehyde concentrations desired for the manufacture of specialty (meth)acrylic acid polymers. In particular, there is a need for a reliable, economical process to provide low furfural and low water (M)AA. More specifically, a need exists for a method of purifying crude (meth)acrylic acid to remove both water and impurities within crude (meth)acrylic acid to produce a high purity (meth)acrylic acid.

In a first embodiment, the present invention relates to a method of purifying crude (meth)acrylic acid by removing water and aldehyde compounds in a distillation system. More specifically, the method of purifying (meth)acrylic acid in accordance with the present invention comprises: directing a (meth)acrylic acid stream containing at least one aldehyde compound to a distillation system; adding at least one aldehyde treating compound capable of reacting with said at least one aldehyde compound to the (meth)acrylic acid stream, such that said at least one aldehyde compound reacts with said at least one aldehyde treating compound to produce a product having a higher boiling point temperature than (meth)acrylic acid; and separating said product from said (meth)acrylic acid stream by distillation such that a purified (meth)acrylic acid stream is produced. In addition, the at least one aldehyde treating compound may be added to the bottom half region of the distillation column of the distillation system, or it may be added to the (meth)acrylic acid stream prior to entering the distillation system. The aldehyde treating compound is selected from the group consisting of sulfuric acid, hydrazine compounds, glycine, lysine, methionine, amine compounds, phloroglucinol, aniline compounds, hydrazide compounds, and mixtures thereof.

The (meth)acrylic acid stream may contain no more than 3000 ppm maleic compounds prior to being directed to said distillation system, or it may contain greater than 3000 ppm maleic compounds. Where the (meth)acrylic acid stream has a concentration of greater than 3000 ppm maleic compounds, the method of the present invention further comprising reducing the concentration of maleic compounds in said (meth) acrylic acid to less than 3000 ppm, prior to directing the (meth)acrylic acid stream to the distillation system, by a process selected from the group consisting of: adding at least a second aldehyde treating compound to said (meth)acrylic acid, distilling the (meth)acrylic acid stream, and adding at least a second aldehyde treating compound to said (meth) acrylic acid stream and distilling said (meth)acrylic acid stream containing said at least a second aldehyde treating compound.

Another embodiment of the present invention is a method of purifying (meth)acrylic acid comprising: directing a (meth)acrylic acid stream containing at least water to a distillation system; adding at least one reactive drying agent to the distillation system, wherein said at least one reactive drying agent is capable of reacting with said water and is selected from the group consisting of acetals, ketals, halogenated anhydrides, isocyanates, 1, 3-phenylene diisocyanate, tetramethoxy-1,4cyclohexadiene, trifluoroacetic anhydride, and combinations thereof, such that said at least one reactive drying agent reacts with said water to produce a product having a higher boiling point temperature than (meth)acrylic acid; and separating said product from said (meth)acrylic acid stream such that a purified (meth)acrylic acid stream is produced. In a further embodiment, the at least one reactive drying agent reacts with the water to produce at least one aldehyde treating compound.

An alternative embodiment of the method of the present invention for purifying (meth)acrylic acid comprises: directing a (meth)acrylic acid stream containing at least water and at least one aldehyde compound to a distillation system; adding at least one aldehyde treating compound capable of reacting with said at least one aldehyde compound to the (meth) acrylic acid stream, such that said at least one aldehyde compound reacts with said at least one aldehyde treating compound to produce a first product having a higher boiling point temperature than (meth)acrylic acid; adding at least one reactive drying agent to the distillation system, wherein said at least one reactive drying agent is capable of reacting with said water such that said at least one reactive drying agent reacts with said water to produce a second product having a higher boiling point temperature than (meth)acrylic acid; and separating said first and said second products from said (meth)acrylic acid stream by distillation such that a purified (meth)acrylic acid stream is produced. The at least one reactive drying agent is selected from the group consisting of acetals, ketals, halogenated anhydrides, isocyanates, 1,3-phenylene diisocyanate, tetramethoxy-1,4cyclohexadiene, trifluoroacetic anhydride, and combinations thereof.

The present invention also includes to a (meth)acrylic acid product comprising less than 1% impurities and less than 5 ppm furfural. The (meth)acrylic acid product may further comprise not more than 0.2 wt % water based on the total weight of the (meth)acrylic acid product. Alternatively, the (meth)acrylic acid product may further comprise not more than 5 ppm acrolein, not more than 5 ppm benzaldehyde, and not more than 5 ppm protoanemonin.

In a further embodiment, the present invention includes a specialty polymer composition comprising units derived from at least the aforesaid (meth)acrylic acid product. Alternatively, the present invention further includes a specialty polymer composition comprising units derived from at least a (meth)acrylic acid product produced by the method of the first embodiment of the present invention.

Still a further embodiment of the present invention relates to a method of purifying a (meth)acrylic acid stream using a distillation apparatus, comprising maintaining the temperature at the bottom of the distillation apparatus at not more than 110° C. At this temperature, the production of methyl vinyl ketone within the distillation apparatus is minimized. Moreover, this method further comprises producing a final product (meth)acrylic acid stream comprising no more than 25 ppm methyl vinyl ketone.

Other and further features and advantages will be apparent from the following description of various embodiments of the invention. These embodiments are given for the purpose of disclosure and may be considered in conjunction with the accompanying drawings.

A more complete understanding of the present embodiments and advantages thereof may be acquired by referring to the following description taken in conjunction with the accompanying drawings, in which like reference numbers indicate like features, and wherein:

FIG. 1 depicts a schematic representation view one embodiment of a method for producing high purity (meth) acrylic acid in accordance with the present invention.

Crude (meth)acrylic acid suitable for use with the method of the current invention may be produced from any number of processes known in the art, such as those mentioned hereinabove. Furthermore, representative examples of such crude (M)AA production processes are disclosed in, but are not limited to, U.S. Pat. No. 6,540,881; EP 1,070,700; U.S. Pat. No. 6,348,638; U.S. Pat. No. 6,399,817, and EP 1,041,062.

Acrylic acid with less than 1% impurities, less than 5 ppm furfural, and not more than 0.05% water is hereinafter referred to as "high purity acrylic cid" or "HPAA." Methacrylic acid with less than 1% impurities, less than 5 ppm furfural, and not more than 0.05% water, is hereinafter referred to as "high purity methacrylic acid" or "HPMAA." Such HPAA and HPMAA products are especially desirable for use in the manufacture of specialty acrylic acid-based and methacrylic acid-based polymers.

The term "(meth)acrylic acid" as used hereinafter refers to both methacrylic acid and acrylic acid and in a like manner the term "(meth)acrolein" refers to both methacrolein and acrolein. Similarly, the term "(M)AA" as used herein is synonymous with the term (meth)acrylic acid.

For simplicity, the purification method of the present invention will be described with respect to acrylic acid. However, it is to be understood that the inventive method of the present invention is equally applicable to methacrylic acid production processes. Additionally, it is understood that the method of the present invention applies equally well to the purification of (M)AA streams derived from processes other than those specifically cited above.

In the embodiment illustrated in FIG. 1, a distillation system 100 having one or more distillation units, such as distillation columns 101, 102, is used to purify a crude acrylic acid stream 1 to a substantially pure, final product acrylic acid stream 7 having low aldehyde content and low water content. More particularly, a crude acrylic acid stream 1 of at least 90% purity is provided to a first distillation column 101. Impurities such as maleic acid and maleic anhydride (hereinafter referred to as "maleic compounds" or "maleics"), are removed from the crude acrylic acid stream 1 in the first column 101. Crude acrylic acid stream 1 can be of typical commercial quality, generally comprising low levels of both acrolein and acetic acid, among other impurities. For example, in the embodiment of FIG. 1, the crude acrylic acid stream 1 comprises less than 30 ppm acolein, less than 1500 ppm acetic acid, less than 8500 ppm maleics, less than 300 ppm benzaldehyde, less than 300 ppm furfural, and less than 0.2% water. The distillation of crude acrylic stream 1 within column 101 produces overhead stream 3 comprising at least purified acrylic acid and a bottoms stream 2 comprising at least maleic compounds.

Although not shown in FIG. 1, Column 101 also includes column ancillaries, wherein the term "column ancillaries" means any and all secondary equipment and associated piping that is connected to a column, such as vacuum equipment, reboilers, condensers, pumps, and process lines including but not limited to feed lines, bottoms lines, overhead lines, vent lines, inhibitor addition lines, oxygen addition lines, reflux lines, and rundown lines.

Column 101 and its column ancillaries are preferably constructed of materials resistant to corrosion. Suitable materials of construction resistant to corrosive effects include but are not limited to: 300 series stainless steel (e.g., 304, 316L, and 317L), 904L, 6-moly stainless steel, HASTELLOY® (e.g., B, B-2, B-3, C-22, and C-276), tantalum, and zirconium. In some embodiments, the manufacturer may reduce construction costs by utilizing covered base metal materials. "Covered base metal" materials are materials that are generally thought not to be corrosion resistant, such as carbon steel, combined with a covering capable of resisting corrosion such as glass, epoxy, elastomer, fluoropolymer (e.g., TEFLON®), or one of the above-listed corrosion resistant metals. Covered base metals are constructed by placing a covering capable of resisting corrosion over, and optionally bonding the covering to, the base metal. The covering prevents contact between the base-metal and the process stream. Covered base-metal construction is especially preferred for large-diameter piping (3.8 cm or larger nominal diameter) and for heat exchanger tubes in high fluid-velocity service (fluid velocity of 0.15 meter/second or more) and other components, where significant metal thickness (3 mm or more metal thickness) may be used to provide structural strength. The materials described above such as 300 series stainless steel, 904L, 6-moly stainless steel, HASTELLOY® (e.g., B, B-2, B-3, C-22, and C-276), tantalum, zirconium, and covered base-metal materials are hereinafter referred to, collectively and in the alternative, as "corrosion resistant material."

Internal components such as trays or packing may be used in column 101, if desired. Such internal components, if present, may be made from the same materials as the column itself or may be constructed from one or more different materials; for example, in one embodiment, column 101 can comprise 316L stainless steel with internals comprising 317L+ stainless steel.

Trays may be used in the first column 101, for example, without limitation, perforated plate trays, since they have been found to be particularly resistant to polymer accumulation. The term "perforated plate trays", as used herein, is meant any tray comprising a planar portion with a plurality of holes through said planar portion. Optional tray features, including but not limited to weirs, downcomers, baffles, distributors, valves, bubblecaps, and drain holes, may also be present. Examples of perforated plate trays include, but are not limited to, sieve trays, dual flow trays, and combination valve and perforation trays. If trays are used in column 101, it is suggested that 35 to 65 perforated plate trays be used.

In one embodiment, for example, the first column 101 comprises at least 39 dualflow trays where the crude acrylic acid stream 1 enters the column below tray number 1 (i.e., the bottommost tray in the column 101). In another embodiment, column 101 comprises at least 50 dualflow trays and the crude acrylic acid stream 1 enters the column 101 at tray number 17 (as counted upward beginning with the bottommost tray). In an alternative embodiment, column 101 comprises at least 63 sieve trays and crude acrylic acid stream 1 enters the column at tray 30.

The first column 101 may be operated at sub-atmospheric pressure to minimize the temperature at the bottom of the column 101. For example, in one embodiment, the pressure at the bottom of the column 101 may be maintained from 95 mmHg to 135 mmHg, allowing the bottom of the column 101 to be operated at temperatures of from 85° C. to 115° C. Embodiments of the method of the present invention include maintaining the bottom of the column 101 at not more than 110° C., or not more than 105° C., or not more than 100° C., and even not more than 90° C. It has been discovered that the minimization of the bottoms temperature in column 101 results in low light ends impurities, such as methyl vinyl ketone (MVK), in overhead distillate stream 4, and subsequently, low light ends content also in the final product acrylic acid stream 7. Embodiments of the product present invention include a final product (meth)acrylic acid stream 7 comprising not more than 25 ppm MVK, or not more than 20 ppm MVK, or not more than 15 ppm MVK, or not more than 10 ppm MVK, and even not more than 5 ppm MVK.

To minimize condensation polymerization, vapor spaces on column 101 and its ancillaries, including condensers and interconnecting vapor lines, may be maintained at a temperature above the dew point of AA. Insulation and electric or steam tracing are effective for this purpose. It is oftentimes useful to add water-soluble or alcohol-soluble polymerization inhibitor to column 101 and its ancillaries to minimize polymerization of AA. Suitable examples of such polymerization inhibitors include but are not limited to: hydroquinone (HQ); 4-methoxyphenol (MEHQ); 4-ethoxyphenol; 4-propoxyphenol; 4-butoxyphenol; 4-heptoxyphenol; hydroquinone monobenzylether; 1,2-dihydroxybenzene; 2-methoxyphenol; 2,5-dichlorohydroquinone; 2,5-di-tert-butylhydroquinone; 2-acetylhydroquinone; hydroquinone monobenzoate; 1,4-dimercaptobenzene; 1,2-dimercaptobenzene; 2,3,5-trimethylhydroquinone; 4-aminophenol; 2-aminophenol; 2-N,N-dimethylaminophenol; 2-mercaptophenol; 4-mercaptophenol; catechol monobutylether; 4-ethylaminophenol; 2,3-dihydroxyacetophenone; pyrogallol-1,2-dimethylether; 2-methylthiophenol; t-butyl catechol; di-tert-butylnitroxide; di-tert-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-dimethylamino-2,2,6,6-tetramethyl-piperidinyloxy; 4-amino-2,2,6,6-tetramethyl-piperidinyloxy; 4-ethanoloxy-2,2,6,6-tetramethyl-piperidinyloxy; 2,2,5,5-tetramethyl-pyrrolidinyloxy; 3-amino-2,2,5,5-tetramethyl-pyrrolidinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; salts of 4-nitrosophenolate; 2-nitrosophenol; 4-nitrosophenol; copper dimethyldithiocarbamate; copper diethyldithiocarbamate; copper dibutyldithiocarbamate; copper salicylate; methylene blue; iron; phenothiazine (PTZ); 3-oxophenothiazine; 5-oxophenothiazine; phenothiazine dimer; 1,4-benzenediamine; n-(1,4-dimethylpentyl)-N'-phenyl-1,4-benzenediamine; n-(1,3-dimethylbutyl)-N'-phenyl-1,4-benzenediamine; n-nitrosophenyl hydroxylamine and salts thereof; nitric oxide; nitrosobenzene; p-benzoquinone; isomers thereof; mixtures of two or more thereof; and mixtures of one or more of the above with molecular oxygen. The polymerization inhibitor(s) may be used alone or combined with a suitable diluent. Suitable diluents include, but are not limited to, (meth)acrylic acid, water, and organic mixtures comprising acetone.

In one embodiment a mixture of HQ/PTZ in acrylic acid solvent is utilized as the polymerization inhibitor in column 101 and its ancillaries. When phenolic inhibitors, such as HQ and MeHQ are used, it is further suitable for oxygen-containing gas to be added to one or more locations throughout the distillation column and its ancillaries to enhance the effectiveness of the inhibitor. The term "oxygen-containing gas," as used herein, refers to any gas comprising from 0.01% up to 100% molecular oxygen. Oxygen-containing gas may be directly mixed with the acrylic acid-containing solution as by bubbling or it may be dissolved in advance in a solvent and the resultant solution used for indirect mixture. The bubbling may be easily accomplished by supplying the oxygen containing gas through the bottom of the distillation column and/or through the reboiler. Molecular oxygen may be generally supplied at a rate in the range of about 0.1-1.0 vol. % and alternatively about 0.2-0.5 vol. %. The dimercaptobenzene; 2,3,5-trimethylhydroquinone; 4-aminophenol; 2-aminophenol; 2-N,N-dimethylaminophenol; 2-mercaptophenol; 4-mercaptophenol; catechol monobutylether; 4-ethylaminophenol; 2,3-dihydroxyacetophenone; pyrogallol-1,2-dimethylether; 2-methylthiophenol; t-butyl catechol; di-tert-butylnitroxide; di-tert-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-dimethylamino-2,2,6,6-tetramethyl-piperidinyloxy; 4-amino-2,2,6,6-tetramethyl-piperidinyloxy; 4-ethanoloxy-2,2,6,6-tetramethyl-piperidinyloxy; 2,2,5,5-tetramethyl-pyrrolidinyloxy; 3-amino-2,2,5,5-tetramethyl-pyrrolidinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; salts of 4-nitrosophenolate; 2-nitrosophenol; 4-nitrosophenol; copper dimethyldithiocarbamate; copper diethyldithiocarbamate; copper dibutyldithiocarbamate; copper salicylate; methylene blue; iron; phenothiazine (PTZ); 3-oxophenothiazine; 5-oxophenothiazine; phenothiazine dimer; 1,4-benzenediamine; n-(1,4-dimethylpentyl)-N'-phenyl-1,4-benzenediamine; n-(1,3-dimethylbutyl)-N'-phenyl-1,4-benzenediamine; n-nitrosophenyl hydroxylamine and salts thereof; nitric oxide; nitrosobenzene; p-benzoquinone; isomers thereof; mixtures of two or more thereof; and mixtures of one or more of the above with molecular oxygen. The polymerization inhibitor(s) may be used alone or combined with a suitable diluent. Suitable diluents include, but are not limited to, (meth)acrylic acid, water, and organic mixtures comprising acetone.

In one embodiment a mixture of HQ/PTZ in acrylic acid solvent is utilized as the polymerization inhibitor in column 101 and its ancillaries. When phenolic inhibitors, such as HQ and MeHQ are used, it is further suitable for oxygen-containing gas to be added to one or more locations throughout the distillation column and its ancillaries to enhance the effectiveness of the inhibitor. The term "oxygen-containing gas," as used herein, refers to any gas comprising from 0.01% up to 100% molecular oxygen. Oxygen-containing gas may be directly mixed with the acrylic acid-containing solution as by bubbling or it may be dissolved in advance in a solvent and the resultant solution used for indirect mixture. The bubbling may be easily accomplished by supplying the oxygen containing gas through the bottom of the distillation column and/or through the reboiler. Molecular oxygen may be generally supplied at a rate in the range of about 0.1-1.0 vol. % and alternatively about 0.2-0.5 vol. %. The amount of molecular oxygen supplied can be based on the amount of the vapor of acrylic acid in the distillation column.

Bottoms stream 2 may be further processed to recover residual acrylic acid. In one embodiment (not shown), bottoms stream 2 is processed in a hydrolytic recovery unit ("HRU")—such as disclosed in U.S. Pat. No. 5,877,345, which is incorporated by reference herein. Further, the bottoms stream 2 leaving the first column 101 can be processed within an acrylate ester production process to recover residual acrylic acid.

As shown in FIG. 1, overhead stream 3 may be at least partially condensed in one or more condensers 104. Between 0% and 100% of the resulting condensed stream can be refluxed to column 101 to obtain the desired purity level of the remaining overhead distillate stream 4 which is conveyed to the second column 102 of the distillation system 100. In one embodiment, overhead stream 3 is condensed using tempered cooling water in the condenser(s) 104 to avoid freezing the acrylic acid in the stream.

In one embodiment, a portion of overhead distillate stream 4 may be re-circulated back (not shown) to the condenser(s) 104 and, optionally, to the vapor inlet line prior to entering the condenser(s) 104, to minimize fouling and improve condenser efficiency. The condensate recirculated from the overhead distillate stream 4 may flow freely out of are-circulation line and into the condenser(s) 104, or it may be applied to the tubesheet, to the condenser interior surfaces, and/or to the inlet vapor line interior walls. If polymerization inhibitor is added to the condenser(s) 104, it may be added through this condensate re-circulation stream to improve the distribution of the inhibitor. In an alternative embodiment, at least a portion of this condensate re-circulation stream may pass through an apparatus that sprays the condensate on the interior surfaces of column 101 and/or its ancillaries to wash off polymerizable condensates.

The overhead distillate stream 4 can comprise up to about 0.5% water. Further embodiments of the method of the present invention utilize an overhead distillate stream 4 comprising not more than 0.30% water, or not more than 0.15% water, or even not more than 0.10% water.

With regard to maleics in the overhead distillate stream 4, this stream can comprise up to about 3000 ppm of maleics. Various embodiments of the method of the present invention utilize an overhead distillate stream 4 having not more than 2000 ppm maleics, or not more than 1000 ppm maleics, or not more than 500 ppm maleics, or even not more than 100 ppm maleics.

Additionally, the overhead distillate stream 4 can comprise up to 100 ppm of protoanemonin (PTA). Various embodiments of the method of the present invention utilize an overhead distillate stream 4 having not more than 50 ppm (PTA), or not more than 30 ppm PTA, or even not more than 10 ppm PTA.

As shown in FIG. 1, overhead distillate stream 4 can be fed to the second distillation column 102 of the distillation system 100 for additional purification.

Optionally, low maleic content crude acrylic acid (stream 10), from a source external to the present process, can be combined with the overhead distillate stream 4 to form a blended final distillation column feed stream 11 comprising not more than 3000 ppm maleics. The term "low maleic content crude acrylic acid" as used herein means a stream of crude acrylic acid comprising less than 3000 ppm maleics. For example, the low maleic content crude acrylic acid stream 10 may be produced by an extractive purification process such as that disclosed, for example, in EP 1,070,700, and which may comprise not more than 1600 ppm maleics, not more than 15 ppm acrolein, not more than 1200 ppm acetic acid, not more than 300 ppm benzaldehyde, and not more than 300 ppm furfural.

The blended feed stream 11 may comprise between 0 and 100% low maleic content crude acrylic acid. In one embodiment, for example, the blended feed stream 11 comprises 100% low maleic content crude acrylic acid (10) and column 101 and its ancillaries are omitted. Alternative embodiments of the method of the present invention employ a blended feed stream 11 comprising less than 50% of stream 10, or less than 35% of stream 10, or less than 15% of stream 10, or even less than 5% of stream 10. Additional embodiments of the present invention include a blended feed stream 11 having not more than about 2000 ppm of maleics, for example not more than about 1000 ppm of maleics.

Blended feed stream 11 is further purified in distillation column 102 to produce a purified vapor stream 6, which is low in aldehydes, such as furfural. The purified vapor stream 6 can be at least partially condensed and between 0 and 100% of the stream may be refluxed to column 102 (as shown in FIG. 1) to obtain the desired purity level of final product acrylic acid stream 7. Such adjustment may optionally take into account the addition rate of any aldehyde treating compounds utilized (as described below) in column 102, and is within the ability of one of ordinary skill in the art of distillation, given the present disclosure. MeHQ or other polymerization inhibitors may optionally be added to final product acrylic acid stream 7 to provide stability in product storage and transport.

Column 102 and its column ancillaries (not shown) are preferably constructed of corrosion resistant material. Internal components such as trays or packing may be used in column 102 if desired. Internals, if present, may be made from the same materials as the column itself or may be constructed from one or more different materials. If perforated plate trays are used, they can comprise from 28 to 42 trays within column 102.

In one embodiment, column 102 comprises at least 29 dualflow trays and blended feed stream 11 enters the column 102 below tray number 1 (i.e., the bottommost tray). In an alternative embodiment, column 102 comprises at least 39 sieve trays and blended feed stream 11 enters the column at tray number 5 (as counted upward beginning with the bottommost tray).

Column 102 may be operated at sub-atmospheric pressure to minimize the temperature at the bottom of the column 102. For example, in one embodiment, the pressure at the bottom of the column 102 may be maintained from 60 mmHg to 100 mmHg; this pressure setting allows the bottom of the column to be operated at temperatures of from 65° C. to 110° C.

It is oftentimes useful to add water-soluble or alcohol-soluble polymerization inhibitor to column 102 and its ancillaries. Examples of suitable polymerization inhibitors include, but are not limited to, those listed hereinabove with respect to column 101. In one embodiment, for example, a mixture of HQ/PTZ in acrylic acid solvent is utilized as the process inhibitor in column 102 and its ancillaries. When HQ inhibitor is used, oxygen-containing gas can be added to enhance the effectiveness of the polymerization inhibitor.

To minimize condensation polymerization, vapor spaces on column 102 and its ancillaries, including condensers and interconnecting vapor lines, can be maintained at a temperature above the dew point of acrylic acid; for example, insulation and electric or steam tracing are effective for this purpose.

In one embodiment of the present invention, purified vapor stream 6 is condensed using tempered cooling water in one or more condenser(s) 106 to avoid freezing the acrylic acid in the stream 6.

Alternatively, a portion of final product acrylic acid stream 7 may be re-circulated back to the condenser(s) 106 and optionally to the vapor inlet line prior to entering the condenser(s) 106. This recirculation can minimize fouling and improve condenser efficiency. The condensate may flow freely out of the re-circulation line and into the condenser(s) 106, or it may be applied to the tubesheet, the condenser interior surfaces, and/or the inlet vapor line interior walls. If polymerization inhibitor is added to the condenser(s) 106, it may be added through this condensate re-circulation stream to improve the distribution of the inhibitor. In another embodiment, at least a portion of this condensate re-circulation stream may pass through an apparatus that sprays the condensate on the interior surfaces of column 102 and/or its ancillaries to wash off polymerizable condensates.

As mentioned previously herein, blended feed stream 11 contains, among other things, impurities (for example, but not limited to, one or more of maleics, acrolein, furfural, benzaldehyde). To facilitate the removal of at least a portion of the aldehydes from blended feed stream 11, at least one aldehyde treating compound is added to blended feed stream 11. As discussed in further detail hereinafter, suitale aldehyde treating compounds are those which are capable of reacting with the aldehydes in blended feed stream 11. The aldehyde treating compound or compounds may be added to blended feed stream 11 by any of various known methods including, but not limited to, introduction of the aldehyde treating compound or compounds to blended feed stream 11 at a point in the process prior to entry into the distillation column 102 (e.g., into the line which conveys blended feed stream 11 to the distillation column 102), or at the same point of entry to the distillation column 102 as where blended feed stream 11 enters the column 102 (e.g., at the same inlet to the distillation column 102 ), or even directly into the distillation column via a different line or inlet from where the blended feed stream 11 enters the distillation column 102. In addition, it is noted that prefixing the aldehyde treating compound or compounds with at least a position of blended feed stream 11 for at least some time period prior to feeding blended feed stream 11 to distillation column 102 may facilitate reaction of the aldehyde treating compound or compounds with the aldehydes present in blended feed stream 11. Such premixing may be suitably accomplished by any of known methods and apparatus, for example, without limitation, use of a static mixer, a dynamic mixer, jet mixing, or turbulent mixing within piping.

Addition of aldehyde treating compounds, in combination with restricting the composition of blended feed stream 11 to not more than 3000 ppm maleics, results in a final product acrylic acid stream 7 that is low in aldehydes and comprising not more than 5 ppm furfural, not more than 5 ppm acrolein, and not more than 5 ppm PTA. In one embodiment, the resulting final product acrylic acid stream 7 comprises not more than 1 ppm furfural, not more than 1 ppm acrolein, and not more than 1 ppm PTA. Such low acrolein, furfural, and PTA levels are especially desirable in the production of superabsorbent polymers.

Because many aldehyde treating compounds may react with maleics as well as other aldehydes (e.g., acrolein, furfural, benzaldehyde), the maintaining the maleic content of blended feed stream 11 to not more than 3000 ppm allows the addition-rate of aldehyde treating compounds to be minimized within the method of the present invention, thereby providing an economic advantage to the manufacturer. An alternative embodiment of the present invention comprises maintaining the maleics content within the blended feed stream 11 to not more than 2000 ppm. Alternative embodiments comprises maintaining the maleics content within the blended feed stream 11 to not more than 1000 ppm, or not more than 500 ppm, or not more than 100 ppm, or even not more than 25 ppm.

Aldehyde treating compounds may be added to the bottom of final distillation column 102 via line 8 (as shown in FIG. 1) or alternatively, admixed with blended feed stream 11 (not shown).

Various compounds suitable for use as aldehyde treating compounds have been disclosed, for example, in U.S. Pat. No. 5,571,386; U.S. Pat. No. 6,228,227; and US 2001/0004960A1, all of which are incorporated by reference herein. Such aldehyde treating compounds include but are not limited to at least one of the following: sulfuric acid, hydrazine compounds, glycine, lysine, methionine, amine compounds, phloroglucinol, aniline compounds, hydrazide compounds, and mixtures thereof.

Hydrazine compounds include, for example, without limitation, the following compounds: hydrazine, phenylhydrazine, hydrazine hydrate, hydrazine sulfate, hydrazine hydrochloride, 4-nitrophenylhydrazine, and 2,4-dinitrophenylhydrazine. Amine compounds include, for example, without limitation, the following compounds: monoethanolamine ("MEA"), ethylenediamine, diethylenetriamine, dipropylenetriamine, and ortho-, para-, and meta-phenylenediamine (i.e., "oPD", "pPD", and "mPD"). Aniline compounds include, for example, without limitation, the following compounds: aniline, and ortho-, para-, and meta-methylaniline. Hydrazide compounds include, for example, without limitation, hydrazides of organic acids and their salts (e.g., carbamic acid hydrazide, semicarbazide hydrochloride), as well as hydrazides of formic acid, acetic acid, propionic acid, butanoic acid and pentanoic acid, and the dihydrazides of adipic acid and succinic acid.

Aldehyde treating compounds may be used alone or in combination with a suitable diluent, such as, for example, low aldehyde content acrylic acid (e.g., HPAA). In some embodiments, the viscosity of the aldehyde treating compounds may be reduced through heating to facilitate delivery by pumping. For example, mPD may be heated to between about 60° C. and about 140° C. to facilitate pumping. Optionally, aldehyde treating compounds may be stored under inert conditions to prevent oxidation. For example, the selected aldehyde treating compounds(s) may be stored in a tank under dry nitrogen or argon.

In one embodiment, at least one aldehyde treating compound is added via line 8 to the final distillation column 102. For example, the at least one aldehyde treating compound may be one or more of oPD, pPD and mPD. Although the at least one aldehyde treating compound may be added to the final distillation column 102 at any point, it is typically added to the bottom half portion of the final distillation column 102, for example, without limitation, at a point below the bottommost tray (i.e., tray number 1). One purpose of adding at least one aldehyde treating compound to the bottom half portion of the column 102 ensures that there is sufficient residence time in the column 102 for the aldehyde treating compound to react with any aldehyde compounds that are present in the (meth) acrylic acid in the column 102. For example, the aldehyde treating compound mPD may be added to the sump 112 of column 102, or to the reboiler circulation line (not shown). The term "sump" as used herein means the region within a distillation column having trays that is below the bottommost tray in the column. One or more of the aldehyde treating compounds listed above may also be, optionally, added to the upper portion of the column via line 9.

Optionally, aldehyde treating compounds may be added to crude acrylic acid stream 1 or directly to column 101 to at least in part reduce the concentration of impurities, such as acrolein and maleics, which may be present in overhead stream 3. Such addition of aldehyde treating compounds to stream 1 or column 101 is herein referred to as 'aldehyde pretreatment'. Embodiments of aldehyde pretreatment include using sufficient amounts of aldehyde treating compounds to reduce the maleic content of crude acrylic acid stream 1 to not more than 12000 ppm maleics, not more than 9000 ppm maleics, not more than 6000 ppm maleics, and not more than 3000 ppm maleics. It will be evident to one of ordinary skill, given the benefit of this disclosure, that in embodiments where the maleic content of crude acrylic acid stream 1 is not more than 3000 ppm maleics, the use of column 101 for removal of maleics may not be required.

Aldehyde pretreatment embodiments include admixing MEA with crude acrylic acid stream 1 or directly into column 101 at a feed rate of from about 0.1 kg MEA/1000 kg of crude acrylic acid stream 1 to about 10.0 kg MEA/1000 kg of crude acrylic acid stream 1. The exact feed rate of aldehyde treating compound will depend, at least in part, on the starting level of impurities in crude acrylic acid stream 1 and reaction-rate controlling factors, such as the reaction temperature and residence time.

For example, in one embodiment of aldehyde pretreatment, the aldehyde treating compound MEA may be admixed with crude acrylic acid stream 1 in a vessel, such as a well-mixed tank or a batch reactor (not shown). It is within the ability of one of ordinary skill in the art to control the residence time within such a vessel though selection of the size of the vessel, as well as adjustments to variables such as flow rates into and out of the vessel. Embodiments of aldehyde pretreatment in a vessel include employing residence times within the vessel of up to 4 hours, up to 8 hours, up to 12 hours, up to 16 hours, and up to 24 hours. Aldehyde pretreatment embodiments may further include maintaining the contents of the vessel at a temperature of up to 25° C., up to 45° C., up to 60° C., up to 80° C., and up to 100° C.

Optionally, different aldehyde treating compounds may be added at two or more locations within the process illustrated in FIG. 1. For example, in the case where aldehyde treating compounds are added via streams 8 and 9, stream 8 may comprise at least one aldehyde treating compound that is not present in stream 9. This method of addition is herein referred to as a "sequential addition" of aldehyde treating compounds. In one embodiment of the present method, for example, wherein sequential addition of aldehyde treating compounds is employed, aniline is added via line 8 and a mixture of MEA and mPD is added via line 9.

In another embodiment, a combination of aldehyde treating compounds comprising at least a first aldehyde treating compound and at least a second aldehyde treating compound may be admixed (not shown) directly into blended feed stream 11. More particularly, the first and second aldehyde treating compounds are selected such that the first aldehyde treating compound is at least partially soluble in the second aldehyde treating compound. For example, without limitation, the combination of aldehyde treating compounds may comprise mPD dissolved into MEA, with or without additional aldehyde treating compounds. Utilizing such a combination of aldehyde treating compounds facilitates their admixture into blended feed stream 11 by minimizing the pre-heating required to render the aldehyde treating compounds capable of being pumped.

Bottoms stream 5, which comprises heavy ends such as PTA and the products resulting from aldehyde treatment, may optionally be further processed to recover residual acrylic acid. In the embodiment of FIG. 1, for example, the bottoms stream 5 is fed to the sump 113 of an optional bottoms stripping column 103 (i.e., below tray number 1 of column 103) for recovery of residual acrylic acid. Bottoms stream 5 may, optionally, be blended with other bottoms streams, and possibly with crude acrylic acid (not shown), as required for optimal economic operation of bottoms stripping column 103.

Bottoms stripping column 103 and its column ancillaries (not shown), if any, may be constructed of corrosion resistant material. Internal components such as trays or packing may be used in column 103, if desired. Internals, if present, may be made from the same materials as the column 103 itself or may be constructed from one or more different materials. Optionally, bottoms stripping column 103 can include from 8 to 18 perforated plate trays. In one embodiment, column 103 comprises at least 17 dualflow trays and bottoms stream 5 enters the column below tray number 1 (i.e., the bottommost tray). In an alternative embodiment, column 103 comprises at least 12 sieve trays and bottoms stream 5 enters the column below tray number 1.

Bottoms stripping column 103 should be operated at sub-atmospheric pressure to minimize the temperature at the bottom of the column. For example the pressure at the bottom of bottoms stripping column 3 may be maintained from 70 mmHg to 110 mmHg, allowing the bottom of the column to be operated at temperatures of from 85° C. to 125° C.

To minimize condensation polymerization, vapor spaces on bottoms stripping column 103 and its ancillaries, including condensers and interconnecting vapor lines, are preferably maintained at a temperature above the dew point of acrylic acid; insulation and electric or steam tracing, for example, are effective for this purpose.

It is oftentimes useful to add water-soluble or alcohol-soluble polymerization inhibitor to bottoms stripping column 103 and its ancillaries. Suitable examples include those listed above with respect to column 101. In one embodiment a mixture of HQ/PTZ in acrylic acid solvent is utilized as the polymerization inhibitor in bottoms stripping column 103 and its ancillaries. When HQ inhibitor is used, oxygen-containing gas can be added to enhance the effectiveness of the polymerization inhibitor.

Vapor stream 12, comprising at least acrylic acid, may be at least partially condensed and between 0 and 100% of the stream 12 is refluxed to bottoms stripping column 103 to obtain the desired purity level of recovered acrylic acid stream 13. In one embodiment, vapor stream 12 can be condensed using tempered cooling water in one or more condenser(s) 106 to avoid freezing the acrylic acid in the stream.

In one embodiment of the present invention, a portion (not shown) of recovered acrylic acid stream 13 may be re-circulated back to the condenser(s) 106 associated with bottoms stripping column 103 and optionally to the vapor inlet line prior to entering the condenser(s) 106. This recirculation of a portion of the acrylic acid stream 13 can help to minimize fouling and improve condenser efficiency. The condensate may flow freely out of the re-circulation line and into the condenser(s) 106, or it may be applied to the tubesheet, condenser interior surfaces, and/or inlet vapor line interior walls. If polymerization inhibitor is added to the condenser(s) 106, it may be added through this condensate re-circulation stream to improve the distribution of the polymerization inhibitor. Alternatively, at least a portion of this condensate re-circulation stream (not shown) may pass through an apparatus that sprays the condensate on the interior surfaces of column 103 and/or its ancillaries to wash off polymerizable condensates.

Recovered acrylic acid stream 13 typically comprises less than 100 ppm furfural, less than 200 ppm PTA, and less than 0.2% water. Such acrylic acid is suitable for many less-demanding applications including acrylate ester production and some emulsion-polymer preparations. Alternatively, recovered acrylic acid stream 13 may be blended with crude acrylic acid in storage, or recycled back to column 101 or 102 to improve overall production yield. Stripped bottoms stream 14 may be further processed to recover residual acrylic acid, for example in a hydrolytic recovery unit (HRU) within an acrylate ester production process.

It has been discovered that if an excess of aldehyde treating compounds are added to column 102 the water content of final product acrylic acid stream 7 will be undesirably increased. This increase in water content can be experienced even though the aldehyde content will be significantly reduced. In such situations of increased water content, final product acrylic acid stream 7 will not attain the desired purity of HPAA. Thus in order to prevent an increase of water content in the final product acrylic acid stream 7, the amount of aldehyde treating compound added should be monitored and controlled.

In one embodiment of the method of the present invention, wherein mPD is the selected aldehyde treating compound, and the maleic content of the blended feed stream 11 is maintained at not more than 1000 ppm, the amount of mPD added to the blended feed stream 11 can range from about 0.5 kg of mPD per 1000 kg of blended feed stream 11 to about 7.0 kg per 1000 kg of blended feed stream 11. Various embodiments of the method of the present invention are possible wherein the amount of mPD added is about 5 kg per 1000 kg of blended feed stream 11, or about 3.5 kg of mPD per 1000 kg of blended feed stream 11, or even about 2.5 kg of mPD per 1000 kg of blended feed stream 11.

In one embodiment of the method of the present invention, the final product acrylic acid stream 7 may be analyzed for aldehyde and water content. Based on the observed aldehyde and water content, the addition rate of aldehyde treating compound may be suitably adjusted to provide the desired acrylic acid product quality. Such adjustments may optionally take into account the amount of condensed overhead stream 6 which is refluxed (returned) to column 102. Such analyses and adjustments are within the ability of one of ordinary skill in the art given the benefit of the present disclosure.

As disclosed herein, the purification process of the present invention is capable of providing a final product acrylic acid stream 7 comprising not more than 5 ppm furfural and not more than 0.05% water—which is a final product stream attaining HPAA purity. It may be advantageous to utilize optional reactive drying agents within the distillation process of the present invention to enhance water-removal efficiency—thereby achieving a final product stream having HPAA purity. Such an enhancement improves process stability and makes it possible to reliably operate the process under economically favorable high-production-rate conditions. It is envisioned that the use of reactive drying agents might also allow water levels substantially lower than 0.05% to be achieved, given the appropriate operating conditions and production rates. By "reactive drying agent" is meant one or more compounds capable of chemical reaction with water thereby minimizing or fully eliminating the water content. More specifically, a "reactive drying agent" may be capable of reacting with water present in the crude (meth)acrylic acid stream to produce a heavy product that has a boiling point temperature higher than (meth)arylic acid, or a (meth)acrylic acid product. For example, acrylic anhydride is capable of reacting with water to form acrylic acid. Where a heavy product is produced it can be separated from the (meth)acrylic acid by conventional separation methods, such as distillation. Alternatively, a "reactive drying agent" may be capable of reacting with water present in the crude (meth)acrylic acid stream to form at least one aldehyde treating compound.

As noted previously, because of its inherent compatibility with the product, acrylic anhydride might be considered a suitable choice for a reactive drying agent for use with acrylic acid in acrylic acid production processes. Surprisingly however, as can be seen from the examples included hereinafter, it has been discovered that anhydrides, such as acrylic anhydride and maleic anhydride, perform poorly with respect to water reduction capability in connection with the method of the present invention for producing (meth)acrylic acid. It is believed that the slow rate of reaction of these anhydrides contributes to their lack of effectiveness as a drying agent. Still more surprising was the discovery that, rather than forming compatible compounds such as acrylic acid, it is instead desirable to use reactive drying agents capable of forming heavy impurities within the acrylic acid purification process. By "heavy" impurities is meant impurities that have a higher boiling point than acrylic acid.

It will be apparent to one of ordinary skill in the art, given the benefit of this disclosure, that any such reactive drying agents selected should also be substantially inert within the method of the present invention. By the term "substantially inert" is meant that the selected agents must avoid negative effects upon the process, which might include but are not limited to, the formation of intractable solids, the inactivation of polymerization inhibitors, the inactivation or consumption of aldehyde treating compounds, the initiation of acrylic acid dimerization or polymerization, the formation of troublesome impurities such as for example acetic acid, and the corrosion of process equipment.

Reactive drying agents suitable for use in the inventive process therefore include one or more selected from the group consisting of acetals, ketals, halogenated anhydrides, isocyanates, and combinations thereof.

Reactive drying agents may be added to one or more locations in the first distillation column 101, the final distillation column 102, or the optional bottoms stripping column 103. For example, reactive drying agents may be admixed with the crude acrylic acid feed stream 1, or may be added through lines 8, 9, or 10. In one embodiment of the method of the present invention, for example, without limitation, tetramethoxy-1,4-cyclohexadiene is added to column 102 via stream 8, and acetal is added to column 102 via stream 9.

In another embodiment of the present method, the reactive drying agent 1,3-phenylene diisocyanate (1,3PD) is added to column 102. Without intending to be limited by theory, it is believed that, upon reaction with water, and in the presence of (M)AA, 1,3PD forms mPD, which can then further react with aldehydes in column 102, thereby reducing the amount of fresh aldehyde treating compounds required. Thus, if used, 1,3PD can be admixed with blended stream 11 or added directly to column 102 via stream 8. Alternatively 1,3PD can be added to column 102 at a molar ratio of about between 0.5:1 and 3:1 with respect to the water concentration in blended feed stream 11. Adjustments to the ratio may be made based on feedback obtained from water analysis of final distillation product stream 7.

EXAMPLES

Reactive Drying Agents

A three-neck round bottom flask was oven dried prior to assembly and the apparatus was purged with dry nitrogen to drive out any water vapor before starting each test. The nitrogen purge was continued during all tests. Each test consisted of adding 150 grams of acrylic acid, inhibited with 200 ppm of PTZ, to the flask. A thermometer was placed into one of the ports of the flask, a condenser (attached to a nitrogen line and bubbler) was placed in the second, and a septum in the third port. The pot was stirred and heated to 90 C, at which point a reactive drying agent of interest was introduced. For ease of comparison, in all examples, a 2:1 molar ratio of drying agent:initial water content in the acrylic acid stream was used. Samples were withdrawn immediately upon drying agent addition and at known intervals thereafter. Samples were immediately frozen in dry ice and analyzed by Karl Fischer titration to determine water concentration.

Example 1 Isocyantes as Drying Agents
1,3-phenylene diisocyanate addition
Water content (wt %)

| 0 min | 5 min | 10 min | 15 min | 20 min | 25 min | 30 min | 60 min | 90 min |
|---|---|---|---|---|---|---|---|---|
| 0.155 | 0.066 | 0.052 | 0.039 | 0.042 | 0.042 | 0.038 | — | 0.031 |

Comparative Example A Carbodiimides as Drying Agents
1,3-dicyclocarbodiimide addition
Water content (wt %)

| 0 min | 5 min | 10 min | 15 min | 20 min | 25 min | 30 min | 60 min | 90 min |
|---|---|---|---|---|---|---|---|---|
| 0.209 | 0.170 | 0.165 | 0.149 | 0.171 | — | 0.169 | 0.157 | 0.141 |

Comparative Example B Orthoformates as Drying Agents
trimethyl orthoformate addition
Water content (wt %)

| 0 min | 5 min | 10 min | 15 min | 20 min | 25 min | 30 min | 60 min | 90 min |
|---|---|---|---|---|---|---|---|---|
| 0.165 | 0.092 | 0.105 | 0.102 | 0.102 | 0.102 | — | 0.124 | 0.139 |

Example 2 Ketals as Drying Agents
tetramethoxy-1,4-cyclohexadiene addition
Water content (wt %)

| 0 min | 5 min | 10 min | 15 min | 20 min | 25 min | 30 min | 60 min | 90 min |
|---|---|---|---|---|---|---|---|---|
| 0.151 | 0.008 | 0.010 | 0.013 | 0.014 | 0.008 | 0.013 | 0.012 | — |

Example 3 Acetals as Drying Agents
acetal addition
Water content (wt %)

| 0 min | 5 min | 10 min | 15 min | 20 min | 25 min | 30 min | 60 min | 90 min |
|---|---|---|---|---|---|---|---|---|
| 0.147 | 0.054 | 0.053 | — | 0.051 | 0.051 | 0.055 | 0.061 | — |

Comparative Example C - Alkyl Anhydrides as Drying Agents
acrylic anhydride addition (0.7% methanol)
Water content (wt %)

| 0 min | 5 min | 10 min | 15 min | 20 min | 25 min | 30 min | 60 min | 90 min |
|---|---|---|---|---|---|---|---|---|
| 0.156 | 0.155 | 0.154 | 0.145 | 0.147 | 0.142 | 0.142 | 0.135 | — |

Comparative Example D - Alkyl Anhydrides as Drying Agents
Maleic anhydride addition
Water content (wt %)

| 0 min | 5 min | 10 min | 15 min | 20 min | 25 min | 30 min | 60 min | 90 min |
|---|---|---|---|---|---|---|---|---|
| 0.154 | — | 0.127 | 0.129 | 0.114 | 0.126 | — | — | — |

Example 4 - Halogenated anhydrides as Drying Agents
trifluoroacetic anhydride addition
Water content (wt %)

| 0 min | 5 min | 10 min | 15 min | 20 min | 25 min | 30 min | 60 min | 90 min |
|---|---|---|---|---|---|---|---|---|
| 0.146 | 0.033 | 0.037 | 0.026 | 0.035 | 0.035 | — | 0.028 | — |

These examples illustrate that acetals, ketals, halogenated anhydrides, and isocyanates are exceptional reactive drying agents that exhibit surprisingly good results for use in the inventive process of the present invention.

It should be noted that epoxides, for example 1,2-epoxyoctadecane, can lead to polymerization of acrylic acid and are therefore not recommended for use as a reactive drying agent in the inventive distillation process.

The present invention described herein, therefore, is well adapted to carry out the objects and attain the ends and advantages mentioned, as well as others inherent therein. While several presently preferred embodiments of the invention have been given for purposes of disclosure, numerous changes in the details of procedures may be made for accomplishing the desired results. For example, the present invention can involve any industrial process having purification of crude methcrylic acid as a part of the process. These and other similar modifications will readily suggest themselves to those skilled in the art, and are intended to be encompassed within the spirit of the present invention disclosed herein and the scope of the appended claims.

The invention claimed is:

1. A method of purifying (meth)acrylic acid comprising:
   a. directing a (meth)acrylic acid stream containing at least (meth)acrylic acid and water and at least one aldehyde compound to a distillation system;
   b. adding at least one aldehyde treating compound capable of reacting with said at least one aldehyde compound to the (meth)acrylic acid stream, such that said at least one aldehyde compound reacts with said at least one aldehyde treating compound to produce a first product having a higher boiling point temperature than (meth)acrylic acid;
   c. adding at least one reactive drying agent to the distillation system, wherein said at least one reactive drying agent is capable of reacting with said water such that said at least one reactive drying agent reacts with said water to produce a second product having a higher boiling point temperature than (meth)acrylic acid, wherein said at least one reactive drying agent is selected from the group consisting of acetals, ketals, halogenated anhydrides, isocyanates, 1,3-phenylene diisocyanate, tetramethoxy-1,4cyclohexadiene, trifluoroacetic anhydride, and combinations thereof; and
   d. separating said first and said second products from said (meth)acrylic acid stream by distillation to produce a high purity (meth)acrylic acid stream comprising less than 1 wt % impurities, less than 5 ppm furfural, and not more than 0.2 wt % water based on the total weight of the (meth)acrylic acid product.

2. The method of claim 1, wherein said at least one reactive drying agent comprises 1,3-phenylene diisocyanate.

3. The method of claim 1, wherein said distillation system includes a distillation column having a bottom half region and wherein said at least one aldehyde treating compound is added to the bottom half region of said distillation column.

4. The method of claim 1, wherein said at least one aldehyde treating compound is added to the (meth)acrylic acid stream prior to entering the distillation system.

5. The method of claim 1, wherein said at least one aldehyde treating compound is selected from the group consisting of sulfuric acid, hydrazine compounds, glycine, lysine, methionine, amine compounds, phloroglucinol, aniline compounds, hydrazide compounds, and mixtures thereof.

6. The method of claim 5, wherein said at least one aldehyde treating compound is meta-phenylenediamine.

7. The method of claim 5, wherein said at least one aldehyde treating compound comprises meta-phenylenediamine and monoethanolamine.

8. The method of claim 5, further comprising the step of mixing the meta-phenylenediamine and the monoethanolamine together prior to adding them to the (meth)acrylic acid stream.

9. The method of claim 1, wherein said (meth)acrylic acid stream contains no more than 3000 ppm maleic compounds prior to being directed to said distillation system.

10. The method of claim 1, wherein said (meth)acrylic acid stream has a concentration of greater than 3000 ppm maleic compounds and further comprising reducing the concentration of maleic compounds in said (meth)acrylic acid stream to less than 3000 ppm, prior to directing the (meth)acrylic acid stream to the distillation system, by a process selected from the group consisting of: adding at least a second aldehyde treating compound to said (meth)acrylic acid stream, distilling the (meth)acrylic acid stream, and adding at least a second aldehyde treating compound to said (meth)acrylic acid stream and distilling said (meth)acrylic acid stream containing said at least a second aldehyde treating compound.

11. A method of purifying (meth)acrylic acid comprising:
   a. directing a (meth)acrylic acid stream containing at least (meth)acrylic acid and water to a distillation system;
   b. adding at least one reactive drying agent to the distillation system, wherein said at least one reactive drying agent is capable of reacting with said water and is selected from the group consisting of acetals, ketals, halogenated anhydrides, isocyanates, 1,3-phenylene diisocyanate, tetramethoxy-1,4cyclohexadiene, trifluoroacetic anhydride, and combinations thereof, such that said at least one reactive drying agent reacts with said water to produce a product having a higher boiling point temperature than (meth)acrylic acid; and
   c. separating said product from said (meth)acrylic acid stream to produce a high purity (meth)acrylic acid stream comprising not more than 0.2 wt % water, based on the total weight of the (meth)acrylic acid product.

12. The method of claim 11, wherein the at least one reactive drying agent reacts with said water to produce at least one aldehyde treating compound.

13. The method of claim 11, wherein said (meth)acrylic acid contains no more than 3000 ppm maleic compounds prior to being directed to said distillation system.

* * * * *